United States Patent [19]

Akiyama

[11] Patent Number: 5,017,008
[45] Date of Patent: May 21, 1991

[54] PARTICLE MEASURING APPARATUS

[75] Inventor: Koichi Akiyama, Tsukuba, Japan

[73] Assignee: Kowa Company Ltd., Japan

[21] Appl. No.: 328,030

[22] Filed: Mar. 23, 1989

[30] Foreign Application Priority Data

Mar. 24, 1988 [JP] Japan .................................. 63-68074

[51] Int. Cl.$^5$ ...................... G01N 15/02; G01N 21/51
[52] U.S. Cl. .................................. 356/336; 356/338; 356/339; 356/246
[58] Field of Search ................ 356/336, 338, 339, 246

[56] References Cited

U.S. PATENT DOCUMENTS 4,673,289  6/1987  Gaucher .......................... 356/246 X Primary Examiner—Davis L. Willis
Assistant Examiner—Matthew W. Koren
Attorney, Agent, or Firm—Bruce L. Adams; Van C. Wilks

[57] ABSTRACT

Disclosed is an apparatus for measuring particles or particulates in a fluid in a measuring cell provided with a measuring window through which a laser beam is projected or through which light scattered from the particles passes. The surface of the measuring window is spherical with a radius of curvature whose center is at a point on which the laser beam converges for measurement. With this arrangement, light focused on the convergence point or light coming from the point always passes through the interface between the window and the fluid in the cell at an angle that is normal thereto. Thus no reflection of the light passing through the window occurs at the interface with the result that fluctuations of the refractive index of the fluid in the cell do not effect the focusing point of the light.

3 Claims, 4 Drawing Sheets

PARTICLE MEASURING APPARATUS

BACKGROUND OF THE INVENTION

1. Field of the Invention

This invention relates to a particle measuring apparatus, and more particularly to a particle measuring apparatus in which a laser beam is projected into a measuring area in a fluid containing particles or particulates to be measured and light scattered from the particles is received and photoelectrically converted into an electrical signal to evaluate particle characteristics such as their size and the number of the particles.

2. Description of the Prior Art

There have conventionally been known measuring techniques in which laser light is projected into a measuring area and the transmission quantity or the scattering characteristics are measured to detect properties such as the size and/or the number of the particles in the measuring area.

For example, one apparatus employs the above mentioned technique in order to measure particle impurities in purified water. The measurement is, however, difficult because the particles in the purified water are very small in size and exist only rarely. Therefore, in order to increase the amount of light scattered by the individual particles, the laser beam from a laser source is focused at an area which is made as small as possible to obtain a high-luminance measuring area. The light scattered from the particles passing through this measuring area are received for measurement.

For the particle measurement in a fluid, it is of importance to reduce the amount of light scattered from the fluid (background light) and to increase the signal portion due to light scattered from the particles. For this reason, Japanese Laid-Open Publication No. 18242/88 (corresponding to U.S. application Ser. No. 072,228 filed on 07/09/87) discloses one such system in which the projected light such as a laser beam is converged in the measuring area with a high convergence factor to increase the intensity of the light and make the light scattered from the particles stronger in intensity. This measuring system also employs a mask having a small aperture to limit the measuring area as viewed from the light receiving side into a field so small as to be able to reduce the background light.

For example, this system is intended to reduce the background light and detect light scattered from the particles smaller than 0.1 microns in diameter. For this purpose, an aperture on the mask is set to be smaller than a few tens of microns in diameter. Thus, it is essential that such a small aperture must always be aligned to an optimal position relative to the converged laser beam of a few tens of microns with extremely high accuracy.

In recent years optical particle measuring system such as the one described above have been applied to measure particle impurities in various kinds of fluids and chemical solutions such as for example, nitric acid or hydrofluoric acid whose refractive index is different from that of water. The change in refractive index of solutions, however, disadvantageously causes a displacement of conjugate relation of the mask relative to the convergence point of the laser beam or condenser lens in the detecting system. In the prior apparatus, this displacement has been adjusted mechanically by moving the mask or lens. This mechanical adjustment for displacement of the conjugate relation between the mask and the convergence point of the laser beam or the lens in the light receiving means is impractical because this adjustment may cause another displacement of the optical axes and also because it requires a rather sophisticated high precision control unit.

Furthermore, if the refractive index of the fluid in the measuring cell varies too greatly, there is the possibility that it influences aberrations of the converging lens or condenser lens, thus greatly reducing the detecting capabilities of the apparatus. The change in refractive index of solutions also affects the scattering intensity, so that a correction is required when the refractive index changes greatly.

SUMMARY OF THE INVENTION

In view of the above problems encountered in the prior art apparatus, it is an object of the present invention to provide a particle measuring apparatus being capable of performing a particle measurement with improved accuracy even if the refractive index of the fluid in the measuring cell changes greatly.

In order to solve the aforesaid problems, the present invention provides a particle measuring apparatus in which a laser beam is projected into a measuring area in a fluid containing particles to be measured and light scattered from the particles is received and photoelectrically converted into an electrical signal to evaluate particle characteristics. The particle measuring apparatus according to the invention comprises a measuring cell containing the fluid which is caused to flow through the measuring area and being formed with a first cell window through which the laser beam is projected and a second cell window through which the light scattered from the particles passes; a laser beam projector for projecting the laser beam through the first window, the laser beam being focused at a convergence point in the measuring area; light receiving means for receiving light scattered from the particles in the measuring area through the second cell window; and means for photoelectrically converting the received light into an electrical signal to evaluate the particles characteristics. In the invention, the second cell window on the measuring cell has its surface made spherical with a predetermined radius of curvature whose center is set at the convergence point.

The inner surface of the cell window defines at least such a spherical surface, but the outer surface may be also spherical with the same condition as that of the inner surface.

Preferably, both the cell window through which the laser beam is projected and that through which the scattered light passes are formed with a spherical surface with a predetermined radius of curvature whose center is positioned at the convergence point.

With such an arrangement, the projected laser beam and/or the light scattered from the particles in the fluid travel along the normal line of the spherical surfaces formed on the measuring cell, so that no refractive function occurs due to the difference of refractive indexes between the cell window and the fluid in the measuring cell, thus causing no effect on the wave front. This allows a particle measurement with improved accuracy even if the refractive indices of the fluid changes greatly.

Thus according to the invention, the conjugate relation between the position of the mask and the converging point of the laser beam remains unchanged even if the refractive index of a fluid changes. Furthermore, this gives no influence on aberrations for the lenses, thus assuring a highly precise measurement also for particles contained in any kind of fluid of different refractive index. The apparatus according to the invention also makes the measurement of the refractive index of the fluid possible, thus allowing a correction for the change in scattering intensity caused by the change in refractive index of the fluid.

BRIEF DESCRIPTION OF THE DRAWINGS

The objects and features of the present invention will become more apparent from the accompanying drawings and the following detailed description of the invention.

DETAILED DESCRIPTION OF THE PREFERRED EMBODIMENTS

Figure 1:
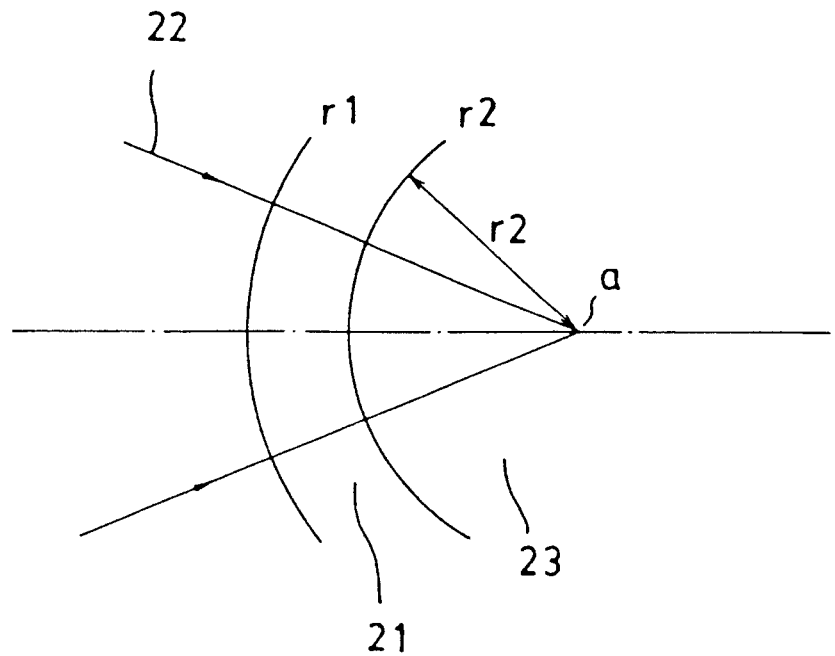
FIGS. 1A and 1B are illustrative views each showing the basic principles and functions of a particle measuring apparatus according to the present invention.
Figure 1:
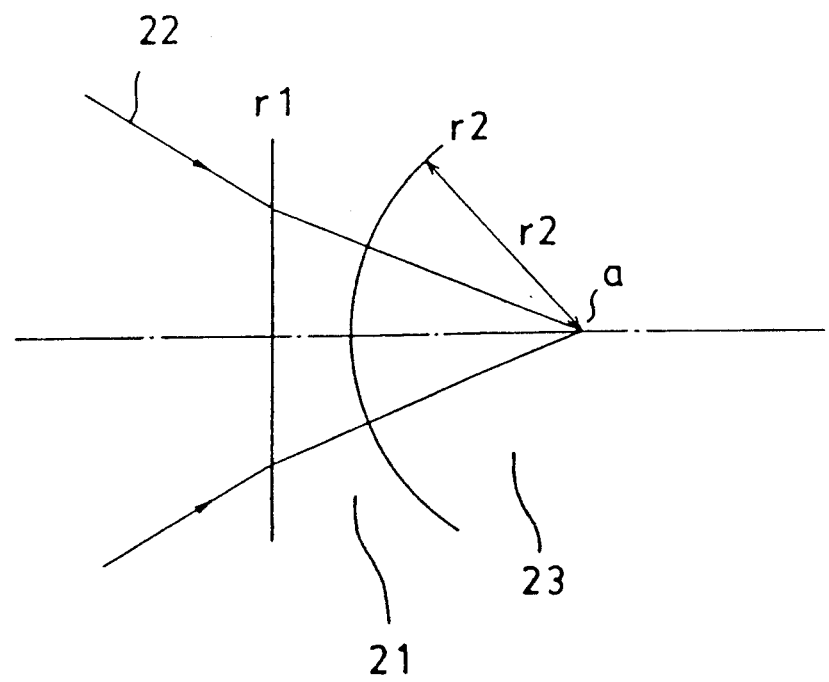

The invention will now be described in detail with reference to the embodiments shown in the drawings.

FIGS. 1A and 1B are schematic representations showing the basic principles and functions of the present invention, in which reference numeral 23 denotes a measuring cell containing a fluid (either liquid or gaseous ) and reference numeral 21 a measuring cell window. The fluid contains particles or particulates to be measured. In the embodiment of the invention, the measuring cell window including a window through which a laser beam is projected and/or a window through which laser light scattered from the particles passes defines a spherical surface with a predetermined radius of curvature whose center is set to a point a on which the laser beam is focused.

The necessary condition is that at least a spherical inner surface r2 of the measuring cell window 21 has a radius r2 of curvature whose center lies at the focus point a of the measuring laser beam. Thus, it may be seen that both flat (FIGS. 1B) and spherical (FIG. 1A) outer surface r1 may be formed in the measuring cell window, but, taking the eccentricity of the cell window into consideration, the spherical surface r1 may be preferable with a radius curvature r1 whose center lies also on the convergence point a.

In such an arrangement, it will be understood that no refraction takes place even if the refractive index of the fluid flowing in the measuring cell varies because a laser beam 22 travels along a path passing through the normal of the spherical surface r2. This causes no change in the propagating wave front and thus no influence on the position of the convergence point and lens aberrations.

The above description is given with respect to the measuring cell window through which the laser beam is projected. It will, however, be understood that the same holds for a cell window through which the laser light scattered from the particles passes.

Figure 2:
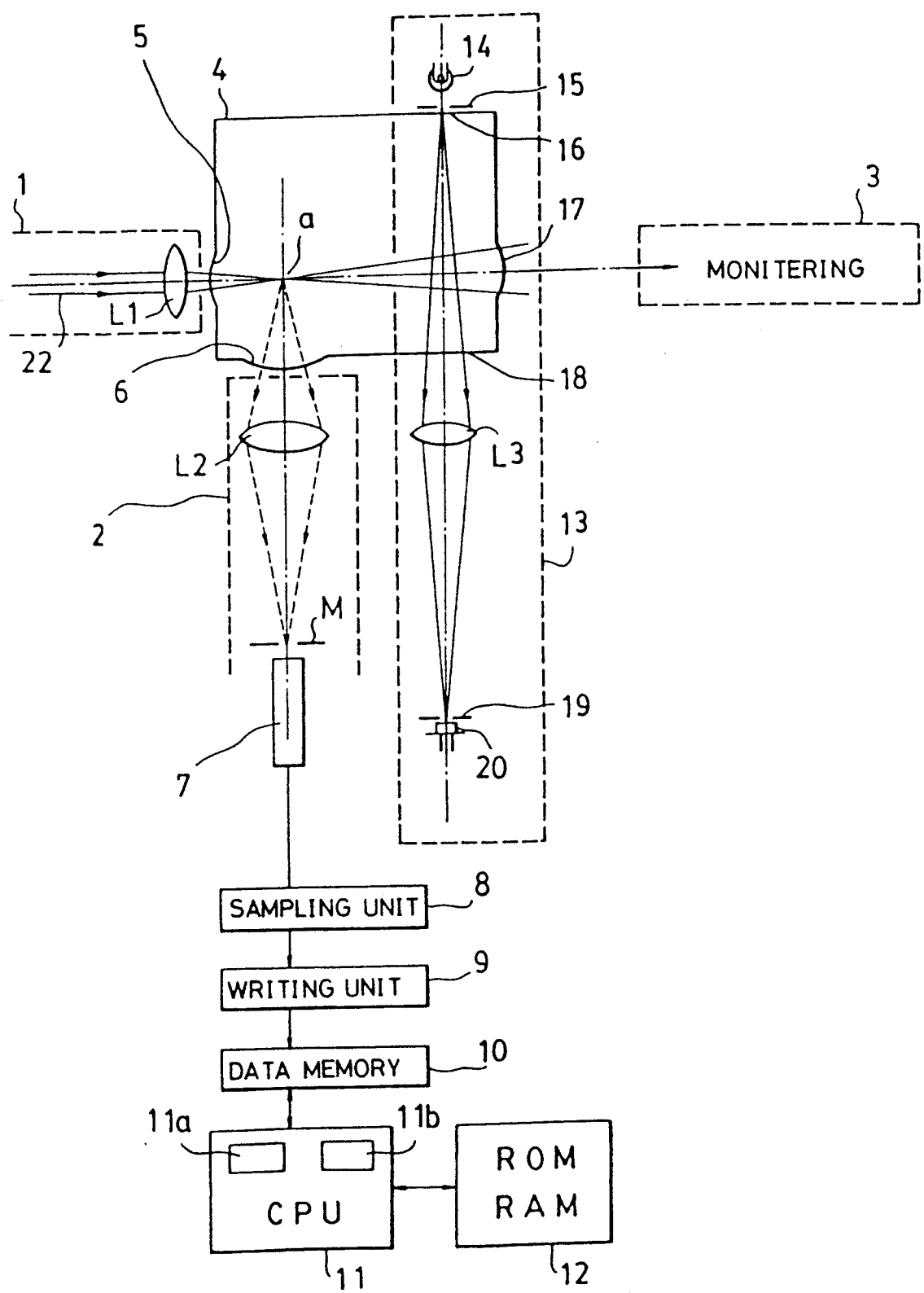
FIG. 2 is a drawing showing an arrangement of the optical system of the apparatus.

Referring now to FIG. 2, the particular embodiment of the present invention will be described in more detail.

In the apparatus shown schematically in FIG. 2, laser light from a laser light source (not shown) is projected through a spherical surface window 5 of a measuring cell 4 and converges at a convergence point a within the measuring cell 4 by means of a converging lens L1 in a laser beam projector 1.

In a similar manner the measuring laser beam is transmitted to a monitoring optical system 3 which includes a spherical surfaced cell window 17. The optical system of the laser beam projector 1 may further include an expander lens (not shown) and other lenses arranged so as to provide desired beam waist and convergence characteristics.

The monitoring optical system 3 functions to detect power fluctuations in the laser and to monitor the alignment of the axis of the laser beam projector. Thus the monitor system is provided so as to allow automatic compensations to be made in accordance with power fluctuations in the laser light source. Further, the monitoring optical system 3 outputs an error message when the measuring beam becomes misaligned.

The fluid (either liquid or gaseous) containing the particles or particulates to be measured is introduced into and drained from the measuring cell 4 in such a manner as to flow past the convergence point a in the measuring area. The fluid may be introduced in any number of directions. The flow path of the fluid may be arranged so as to coaxial to the measuring laser beam, may be perpendicular thereto, or may be parallel to the axis of the scattered light detecting means or perpendicular thereto, that is, perpendicular to the plane of paper. To improve the measurement accuracy, the fluid may preferably be introduced so that the flow path is oblique at a predetermined angle with respect to the above-mentioned directions.

When a particle suspended in the fluid in the measuring cell passes through the convergence point a of the measuring laser beam, it scatters the laser beam. A portion of the scattered laser beam passes through a light receiving system 2 and converges on an aperture of a mask M so as to form an image of the convergence point a thereon. For measurement purposes the portion of the light that passes through the aperture of the mask M is incident on a photoelectric detector 7 comprised of, for example, a photomultiplier.

In the example shown in FIG. 2 the measuring cell windows 5, 6 and 17 are all of the variety in which they have a spherical surface whose center of radius of curvature is at the convergence point a in the measuring cell. The most critical window is the window 6 through which the scattered laser light passes, so that it is preferable that at least the window 6 may be formed with a spherical surface in accordance with the invention.

Connected to the photoelectric converter 7 is a sampling unit 8 for integrating in unit sampling intervals photoelectric pulses which are produced from the photoelectric detector 7, corresponding to the intensity of the scattered light. The output of the sampling unit 8 is then fed to a writing unit 9 for writing values counted in sampling intervals as time series data. The time series data from the writing unit 9 are stored in a time series data memory 10. A central processing unit is further provided which controls the time series data memory 10, a ROM for storing programs and a work area memory (RAM) 12 for storing processed data.

Figure 3:
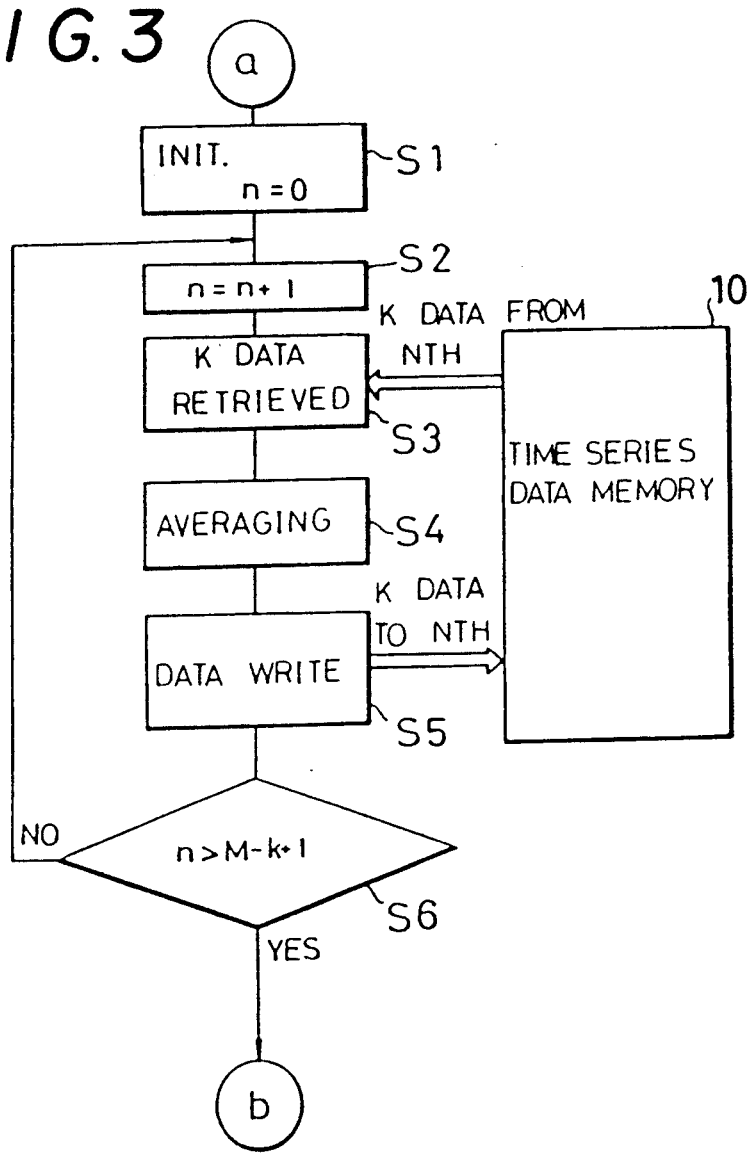
FIG. 3 is a flow chart showing the operation of the apparatus shown in FIG. 2.

FIG. 3 shows a flow chart which illustrates how the apparatus according to the invention operates.

As shown in FIG. 2, the laser beam 22 is converged on the point a through the spherical cell window 5. The fluid containing the particles to be measured is caused to pass through a particle measuring area including the convergence point a at its center. The light scattered from the particles in the measuring area passes through the spherical cell window 6 and is focused on the the mask M by means of the converging lens L2. The scattered light passing through the mask aperture impinges on the photoelectric detector 7. The photoelectric pulses corresponding to the scattered light and produced from the photoelectric detector 7 are integrated in unit sampling intervals by means of the sampling unit 8 and then stored in the time series data memory 10.

In cases where the photoelectric detector is comprised of a photomultiplier type photon counter, the photosensing unit is subject to probability-related fluctuations due to its extremely high sensitivity. Therefore, running average calculations are performed for the data in the memory 10 in order to determine the average light intensity at the position of the mask M as shown in FIG. 3.

After initiating the process at step S1, the address from which data is to be read out is incremented at step S2. At step S3 k data from the n-th data are read out from the memory 10. At step S4 an average operation is performed for the k data. The data for which the average operation is carried out are returned for storage to the address n in the time series data memory 10 at step S5. This process is repeated to effect the running average for the time series data stored until $n > N - k + 1$ is satisfied at Step S6, wherein N is the total number of data.

As has been mentioned above, the spherical surface of the measuring cell window has a radius of curvature whose center is set to coincide with the convergence point a in the measuring cell. The laser beam thus can advance along the normal of the spherical surface even if the refractive index of the fluid in the measurement cell changes, thus assuring a particle measurement with high accuracy without any refraction.

In the above mentioned embodiment, the change in the refractive index of the fluid causes a change in focal length of the entire optical system including the radius r1 of curvature of the outer surface and the radius r2 of curvature of the inner surface in the measuring cell. This also causes a change in spot size of the laser beam at the convergence point and a change in the magnification factor of the lens for an image projected on the mask M.

Assume that $f_0$ is the focal length of the entire system for the measuring cell full of air (1.0 refractive index) and $f_n$ the focal length of the entire system for the measuring cell having the refractive index n of the fluid. Then, $$f_n = f_0/n \tag{1}$$

holds. Thus for the change in spot diameter on the side of the converging lens, the following holds $$\omega_0' = \omega_0/n \tag{2}$$

wherein $\omega_0$ is the beam waist diameter when the measuring cell is full of air and $\omega_0'$ the beam waist diameter when the refractive index of the fluid in the cell is n.

On the other hand, the projection magnification at the mask may be calculated according to the Lagrange-Helholts formula:

$$\alpha' = n.\alpha \tag{3}$$

wherein $\alpha$ is the lateral magnification at the mask when the measuring cell is full of air and $\alpha'$ is the lateral magnification at the mask when the refractive index of the fluid in the cell is n.

Upon comparison of formulas (2) and (3), it may be seen that there is no relative change in the beam waist diameter and the projection magnification at the mask. It is therefore not necessary to change the size of aperture of the mask M. On the other hand, the size of the image on the mask and the beam waist diameter do change in terms of their absolute values. Therefore, the luminous intensity of the scattered light and the detected value thereof fluctuate as a function of n. For this reason, it is necessary to measure the absolute value of the refractive index n when its value changes radically.

Figure 4:
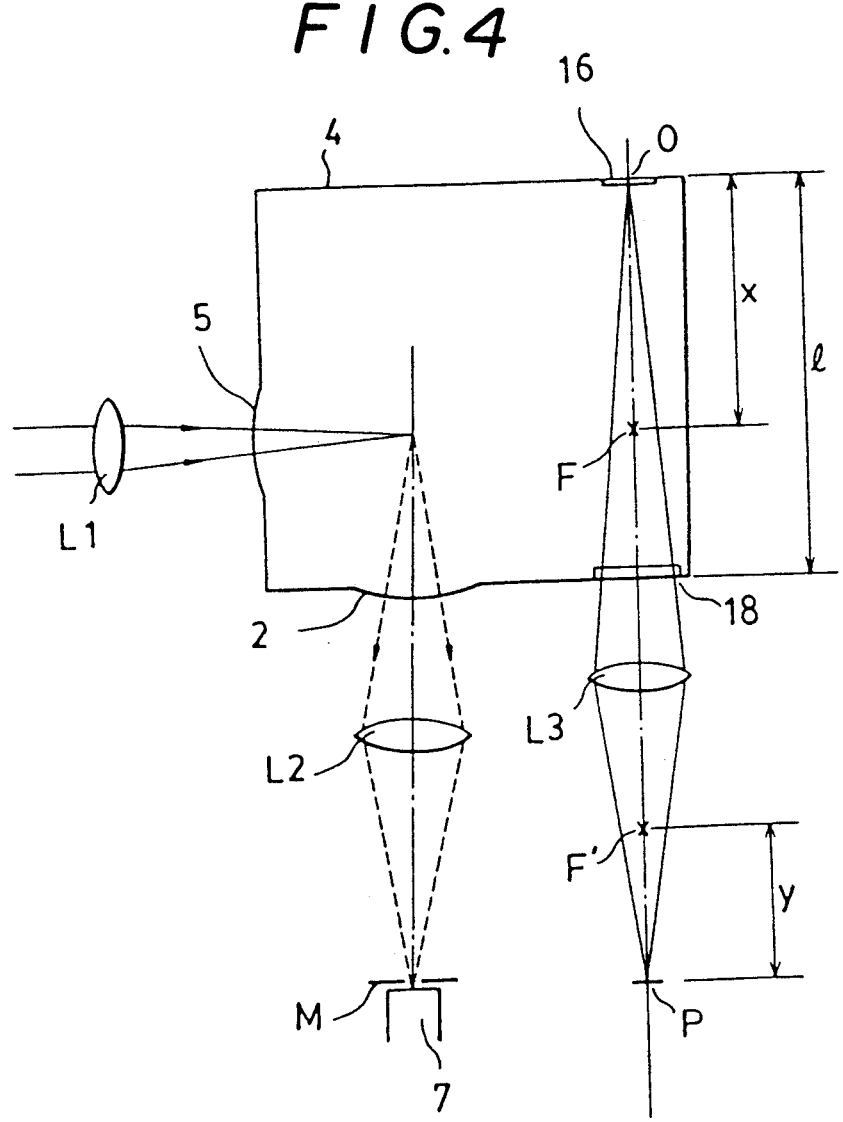
FIG. 4 is a view showing an arrangement in which a refractive index of a fluid is measured.
Figure 5:
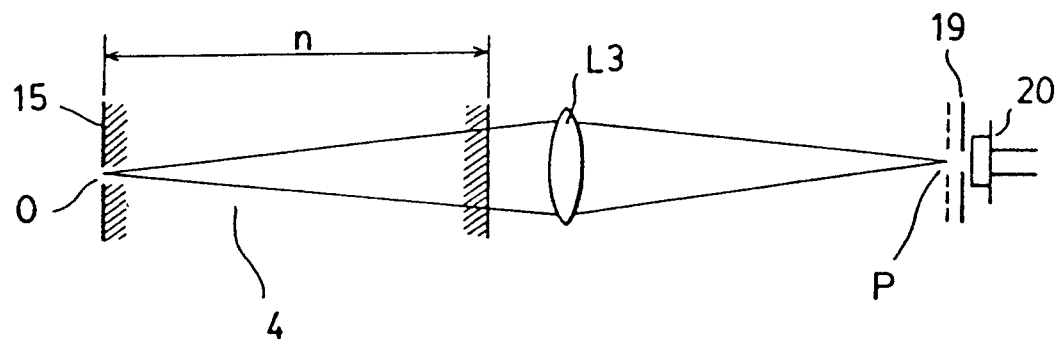
FIG. 5 is an illustrative view showing the basic principle of the refractive index measurement.

For this reason, the apparatus according to the invention is provided with an optical system for measuring the refractive index as shown in FIGS. 4 and 5.

A pin hole 15 illuminated by a light source 14 such as a light emitting diode or the like is focused on a pin hole 19 by a lens L3 through a flat cell window 16, a measuring cell 4 and a flat cell window 18. The image of the pin hole 15 with its amount of light limited by the aperture of the pin hole 19 reaches a photoelectric converter 20 such as a photodiode or the like. The pin hole 19 is constructed to be movable along the direction of the optical axis together with the photoelectric converter 20. When the refractive index in the cell changes the pinhole 19 together with the photoelectric converter 20 is displaced to measure the refractive index.

When the measuring cell is full of air, the image of the pin hole 15 and the aperture defined by the pin hole 19 assume a relationship in which the image of the pin hole 15 is larger than or equal to the aperture of the pin hole 19.

Particularly, the refractive index n can be calculated as follows:

Assume that the units or elements occupy a position as shown in FIG. 4 with the refractive index of 1.0 (air) in the cell and a focal length f of the lens L3, then according to the Newtons law the following holds $$x.y = f^2 \tag{4}$$

When the refractive index in the cell is n and the distance traveled by an image point P is delta y, then $$\{x - (L - (L/n))\}.(y + delta\ y) = f^2 \tag{5}$$

Solving this equation in terms of n, $$n = L(y + delta\ y)/\{f^2 + (L - x)(y + delta\ y)\} \tag{6}$$

(when $n = 1$, delta $y = 0$)

This shows that the measurement of delta y determines the value of the refractive index n.

It will be noted that, in FIG. 4, points F and F' are the focal points of the lens L3 and the point P is an image of an object O formed by the lens L3.

For the measurement, the pin hole 15 with a diameter M is located at the object point O and the photodiode 20 provided with the pin hole 19 having a diameter N is located at the image point P as shown in FIG. 5.

Assuming that $\alpha_0$ is a lateral magnification from the object point O to image point P for the air in the cell and $\alpha_n$ a lateral magnification for a medium in the cell having the refractive index n, then $\alpha_n$ is always greater than or equal to $\alpha_0$ for the refractive index n which is greater than or equal to 1.0. If the diameter N is now determined so as to be smaller than or equal to $M.\alpha_0$, the diameter N is always smaller than or equal to $M.\alpha_n$. Thus by moving the pin hole of the mask 19 to the point at which the best focus is obtained, the maximum detected light value is obtained and thus by determining this focal point the refractive index of the fluid in the cell may be determined.

Figure 6:
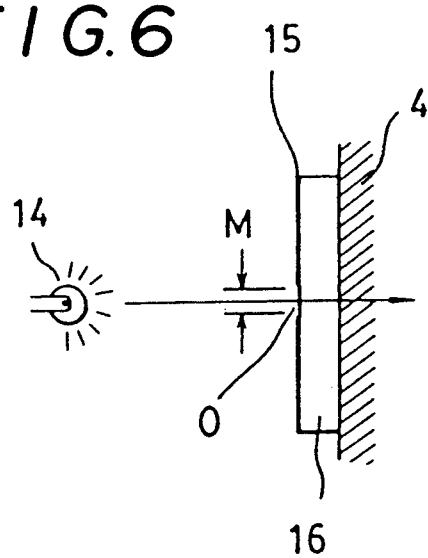
FIG. 6 is an illustrative view showing how a pin hole serving as a chart is illuminated at the time of refractive index measurement.

In order to carry out the above mentioned measurement, a pin hole is formed in the manner as shown in FIG. 6. The pin hole mask 15 having an aperture diameter of M is formed by way of vapor deposition or by chromium plating on a transparent substrate 16 to interrupt the light from the light source other than the light passing through the aperture M. The substrate 16 may be comprised of a transparent material such as quartz, glass, pyrex or other suitable material. The pin hole 15 having the diameter M may alternatively be adhered to the planer surfaced window 16. The thus formed pin hole 15 is illuminated by the light source 14, which may be turned off or blinded by a shutter during the particle measurement.

The great magnification of a projected image from the points O to P improves the accuracy in measurement. For this reason the magnification may be determined depending upon its demand. Too great a magnification would, however, be not preferable because the focal depth is also too deep.

Thus it will be appreciated that the apparatus according to the invention is preferably provided with an optical system for measuring the refractive index for the purpose of correction.

The apparatus according to the invention indeed needs an additional refractive index measuring system in comparison with the prior art apparatus, but no adjustment is advantageously required for the particle measuring apparatus and no lens aberration occurs even if fluctuations in the refractive index of the fluid takes place. This also means that fluctuations in the refractive index of the fluid can not be detected by means of the particle detecting optical system and thus the refractive index measuring system is additionally needed.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A particle measuring apparatus in which a laser beam is projected into a measuring area in a fluid of a predetermined refractive index containing particles to be measured and light scattered from the particles is received and photoelectrically converted into an electrical signal to evaluate particle characteristics, comprising:

a measuring cell for containing a fluid which is caused to flow through the measuring area and having a first cell window through which the laser beam is projected and a second cell window through which the light scattered from the particles passes;

a laser beam projector for projecting the laser beam through said first window, said laser beam being focused at a convergence point in the measuring area;

light receiving means for receiving light scattered from the particles in the measuring area through said second cell window;

means for photoelectrically converting the received light into an electrical signal to evaluate characteristics of the particles;

wherein said second cell window on the measuring cell has a spherical surface with a predetermined radius of curvature whose center is set at the convergence point; and means for measuring the refractive index of the fluid in the measuring cell.

2. An apparatus as set forth in claim 1, wherein said first cell window on the measuring cell also has a spherical surface with a predetermined radius of curvature whose center is set at the convergence point.

3. An apparatus as set forth in claim 1, wherein said means for measuring the refractive index of the fluid comprises a light source for illuminating a first pin hole serving as a chart, a lens for forming an image of the pin hole onto a second pin hole having an aperture which is smaller than or equal to the image of the first pin hole when air is in the measuring cell, and a photoelectric converter disposed behind the second pin hole.

* * * * *